US008741218B2

(12) United States Patent
    Saito

(10) Patent No.: US 8,741,218 B2
(45) Date of Patent: Jun. 3, 2014

(54) AUTOMATIC ANALYZER

(75) Inventor: Michihiro Saito, Kashiwa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 233 days.

(21) Appl. No.: 13/145,346

(22) PCT Filed: Dec. 14, 2009

(86) PCT No.: PCT/JP2009/006827
§ 371 (c)(1),
(2), (4) Date: Aug. 10, 2011

(87) PCT Pub. No.: WO2010/086942
PCT Pub. Date: Aug. 5, 2010

(65) Prior Publication Data
US 2011/0293473 A1    Dec. 1, 2011

(30) Foreign Application Priority Data
Jan. 29, 2009  (JP) .................................. 2009-017465

(51) Int. Cl.
    *G01N 33/00*    (2006.01)
(52) U.S. Cl.
    USPC .............................. 422/52; 422/68.1; 422/500
(58) Field of Classification Search
    USPC .......................................... 422/52, 68.1, 500
    See application file for complete search history.

(56) References Cited

U.S. PATENT DOCUMENTS

2006/0078929 A1    4/2006  Bickel et al.

FOREIGN PATENT DOCUMENTS

| JP | 6-65862 U | 9/1994 |
|---|---|---|
| JP | 11-326334 A | 11/1999 |
| JP | 2003-1465 A | 1/2003 |
| JP | 2003-57239 A | 2/2003 |
| JP | 2006-523095 A | 10/2006 |
| JP | 2007-171213 A | 7/2007 |
| JP | 2008-304275 A | 12/2008 |

*Primary Examiner* — Sam P Siefke
(74) *Attorney, Agent, or Firm* — Mattingly & Malur, PC

(57) ABSTRACT

An analytic method uses a labeled antigen, labeled antibody, tracer, etc. in which a radio isotope, fluorescent dye, luminescent dye, enzyme, etc. is bonded to an antibody or an antigen bonded to a protein as an object of analysis for performing an assay of a trace amount of a substance such as a hormone, tumor marker, infective pathogen marker, infective antibody, etc., for blood, serum, plasma, or body fluid as a sample or specimen. The analysis is enabled at high sensitivity, with less generation of noises and at low background. When an assay is performed based on the antigen-antibody reaction for a sample in an analytic method by fluorometry or luminometry, detection or measurement of non-specific fluorescence or luminescence such as interference light is eliminated or removed effectively irrespective of the property of the sample or the level of the concentration of substances contained in the sample.

10 Claims, 5 Drawing Sheets

MEASUREMENT AT 5 MIN   MEASUREMENT AT 10 MIN   MEASUREMENT AT 15 MIN

AUTOMATIC ANALYZER

TECHNICAL FIELD

The present invention relates to a method of analyzing an antigen or antibody for blood, serum, or plasma as a sample or a specimen by utilizing antigen-antibody reaction using a fluorescent substance or a luminescent substance bonding to an antigen or an antibody for the purpose of determining the presence or absence of reaction and the amount of reaction upon analysis of trace substances in blood.

BACKGROUND ART

In a trace substance assay of hormone, tumor marker, infectious pathogen marker, infective pathogen antibody, etc. for blood, serum, plasma, or body flood as a sample or a specimen, there has generally been used a method of qualitatively or quantitatively detecting proteins, etc. in the sample or the specimen by bonding based on antigen-antibody bonding reaction on every analysis items of proteins. The antibody or the antigen bonding to a protein as an object of analysis in this case is bonded with a radioactive isotope, fluorescent dye, luminescent dye, enzyme, rare earth complex, metal ion, etc. and referred to as a labeled antigen, a labeled antibody, or a tracer.

Similarly, for the assay of DNA or RNA, for example, of a pathogen, a drug metabolizing marker, etc. in the sample or the specimen, a DNA chain or an RNA chain complementary to the DNA or RNA of an object of analysis is hybridized to detect the object of analysis. In this instance, the complementary DNA chain or RNA chain is labeled directly or indirectly with a fluorescent substance or a luminescent substance.

Immunoassay is a specific measuring method of a biological substance on the basis that an antigen and an antibody bonded thereto form antigen-antibody bonding. The method includes a solution precipitation reaction method, a carrier agglutination reaction method, and a labeled antibody method based on the principle of measurement. The solution precipitation reaction method is a method of optically measuring and determining agglutinates formed by the antigen-antibody bonding in a solution, for which immuno turbidimetry, immuno nephelometry, etc. are known. The carrier agglutination reaction method is a method of subjecting a carrier such as an antibody-immobilized latex and a sample solution (antigen) to antigen-antibody bonding and measuring and determining the resultant agglutinates of the carrier optically or imagewis. The carrier agglutination reaction method measures apparent particle diameter or decrease or increase in the transmission light by latex turbidimetry, a latex nephelometry, particle counting, image processing, etc. The labeled antibody method is a method of using an antibody labeled with various labeling substances to subject the same to antigen-antibody bonding, and measuring only the ingredient reacted with the labeled antibody. The labeled antibody methods known include radioimmunoassay, enzyme immunoassay, fluorescent immunoassay, chemiluminescent immunoassay, electroluminescent immunoassay, etc. based on the labeling substances.

Problems pointed out for the immunoassay are to be set forth below.

1. Effect by heterophil antibody: In the system where a monochronal antibody is used as the antibody, when HAMA (human anti-mouse antibody) is present in the sample, it crosslinks a labeled antibody and an immobilized antibody, resulting in false-positive.

2. Non-specific reaction with blocking agent, etc.: A blocking agent or a protective protein contained in a reagent reacts with substances in the sample, resulting in false-positive.

3. Non-specific reaction with labeled enzyme: When a substance bonding to a labeled enzyme is present in the sample, background increases.

4. Prozone phenomenon or high dose huck: When the concentration of an antigen is higher than a measurement range or when the concentration of a labeled antibody greatly exceeds the measurement range, false-negative occurs. In an antigen excessive region, an antigen-antibody complex becomes soluble to sometimes show an abnormally low value.

5. Effect of hemolysis: When hemolysis in the sample is intense, this results in influence on the color formation upon judgment to make the judgment difficult.

6. When faces and urine are used as the sample: Fresh samples are used. Samples containing intense turbid urea or blood cells are not suitable.

7. Effect due to the property of sample: When the viscosity of the sample, particularly, the concentration of protein (M protein, cryoglobulin positive sample) is high, the reaction rate is low and false-negative occurs. Test is performed again by using a diluted sample. Non-specific scattering sometimes occurs due to the presence of milky serum or immuno complex.

8. False-positive and false-negative due to crossed reaction: They are observed in a system in which a recombinant antigen is used. Further, false-positive is shown by crossed reaction in FSH, TSH, and LH.

9. Effect of drugs used (atropine, caffeine, acetoamidephenol, acetylsalicylic acid, ascorbic acid, etc.): False-positive is shown due to the effect of drugs in a urine hCG measuring system.

10. Inter-reagent difference of measuring sensitivity: In some cases, while the reaction shows negative for a predetermined judging time, positive reaction develops with lapse of time.

Long time has been elapsed since Berson and Yalow completed radio immunoassay by labeling radioactive isotopes to antigens or antibodies. This is used still at present as a useful method in view of the good sensitivity and high specificity. Meanwhile, development and improvement have been made for enzyme immunoassay, fluorescent immunoassay, luminescent immunoassay, etc.

The enzyme immunoassay is a method of labeling an enzyme, instead of the radioactive isotope, to an antigen or an antibody, which enables measurement at high sensitivity in view of the high catalytic activity of the enzyme to a substrate.

A time-resolved fluorometry of pulsatively irradiating a final product of antigen-antibody reaction with exciting light and, after lapse of a time in which fluorescence generated from a reaction vessel, etc. is quenched, measuring the fluorescence of the substance has been developed. In recent years, europium complexes or samarium complexes having relatively long fluorescence quenching time or not requiring sensitizer have been developed and the method has become more effective.

In the luminescent immunoassay, a method of labeling isoluminol or acridinium ester and measuring the amount of luminescence is provided, and measuring systems according to following combinations are established: a combination of peroxidase and luminol using a substrate capable of luminescent reaction while using an enzyme as the labeling substance, or a combination of a substrate such as AMPPD that emits light when a phosphoric acid group is dissociated and an alkali phosphatase, or a combination of using luciferase as a labeling substance and using luciferin as a substrate.

In labeled antigen, labeled antibody, labeled DNA, labeled RNA, tracer, etc., while a single fluorescent substance or luminescent substance is bonded to a material to be labeled, it has been attempted to bond many fluorescent substances or luminescent substances to a material to be labeled for the purpose of increasing the amount of fluorescence or luminescence. A plurality of fluorescent substances or luminescent substances are formed as a complex, as a complex with bovine serum albumin, streptavidin or like other protein, or bonded to the surface of a fine particle, and they are bonded as a labeling material to the material to be labeled. For the fine particle, particles of gelatin, latex, or polystyrene having a diameter of about 2 micrometer (μm) are generally used, serving as a carrier for the fluorescent substance or the luminescent substance. In recent years, finer particles of about 100 nanometer (nm) diameter have also been developed. Further, for the bonding or immobilization of the fluorescent substance or the luminescent substance to the carrier, the fine particles and the fluorescent substance or the luminescent substance are often mixed in a buffer solution and bonded by electric bonding.

The reaction surface as a site for the antigen-antibody reaction or gene detection method generally comprises a flat plate or particle of a plastic or glass material, and magnetic particle incorporating iron oxide is also used. Further, filter, woven fiber, multi-layered paper, porous film, etc. are sometimes used for increasing the surface area for immobilization.

When individual bodies having the reaction surface are particles, they are put into a reaction vessel and mixed with a sample or a specimen or a reagent, and cells, microtiter plates, etc. made of transparent mineral ores such as quartz or artificial stone thereof, glass, or compounds such as polycarbonate material, polystyrene material, and polyvinyl material are used as the vessel.

A method of measuring items in immuno serum assay for clinical inspection often includes a method of detecting an antigen-antibody reaction by using an antibody or an antigen having a fluorescent substance or a luminescent substance as a labeled substance by utilizing the reaction. In this case, the antigen-antibody reaction is detected also even if the fluorescent substance or the luminescent substance such as a dye, fluorescent dye, or phosphorescent dye is labeled directly to the antibody or the antigen. However, when labeled antibody or antigen is prepared by bonding a plurality of substances to a labeling carrier thereby forming a complex of a fluorescent substance or a luminescent substance and a carrier and binding the same to an antigen or antibody, the number of the fluorescent substance or the labeled body bonding to one molecule of the antigen or the antibody can be increased to generate more intense signals. When proteins such as bovine serum albumin and keyhole limpet hemocyanine, particles of plastics, for example, of polystyrene and polypropylene, ferrite, silica, gelatin and other polymerization products, or chained carbon compounds such as polyvinyl alcohol are used, they correspond to the labeling carrier.

Alternatively, a plurality of fluorescent substances or luminescent substances can be sealed in liposomes, lipid films, or hollow plastic materials thereby capable of amplifying signals. In this case, the liposomes, lipid films, or hollow plastic materials correspond to the carrier.

The carrier is formed as a complex with the fluorescent substance or the luminescent substance and used as a labeling material. The labeling material sometimes forms a macro agglutinate block during preservation. Further, the thermal stability lowers remarkably by the formation of the complex, and the material also tends to be adsorbed easily to a reaction vessel or the reaction material for immobilization to result in increase of non-specific background. In the same manner, due to the property of the carrier and the labeling substance and, further, the ingredients contained in the solution, extinction or quenching occurs that reduces color formation, luminescence or fluorescence of a substance. Further, when the antigen or the antibody is labeled, since the molecule of the labeled material is large, the antigen-antibody reaction is remarkably lowered.

In the antigen-antibody reaction by fluorometry or luminometry, the fluorescent substance, the luminescent substance, or the enzyme bonded to the labeled antibody or the labeled antigen is not bonded to the antibody or the antigen in 1:1 relation but a plurality of molecules of the fluorescent substance, the luminescent substance, or the enzyme are generally bonded to one molecule of the antibody or the antigen. It is intended to takeout signals under amplification.

The fluorescent substance, the luminescent substance, or the enzyme is bonded in plurality to other protein or support, and the protein or the support is used as the carrier for the fluorescent substance, etc. It is important that the carrier satisfy the following requirements.

1. Preferably, the carrier has a large surface area while the molecular weight is low and has a specific gravity about equal to that of a buffer to be used.
2. Preferably, the carrier tends to immobilize the fluorescent substance, etc. and does not lower the fluorescence or the luminescence of the fluorescent substance, etc.
3. Preferably, the carrier less adsorbs to a reaction vessel or other particles after labeling of the fluorescent substance, etc. to the carrier.
4. Preferably, the carrier is fine and has such a size not to optically interrupt excitation light and, in the same manner, does not hinder the detection of the fluorescence or the luminescence at a photomultiplier or the like. If an object shorter than a wavelength is present, the carrier does not interrupt the light. When the carrier is shorter than the wavelength of the light to be used, the light transmits the carrier without decay when it does not transmits the carrier. Further, light is not scattered by the carrier and generation of noises is minimized.
5. Preferably, the carrier is colorless and transparent and does not hinder the transmission of excitation light. Preferably, the carrier does not generate non-specific fluorescence or luminescence by the irradiation with the excitation light.
6. Preferably, the carrier has high hydrophilicity and high dispersibility. In the same manner, it preferably maintains high hydrophilicity and dispersibility easily after labeling the fluorescent substance, etc.

A homogeneous measuring method (homogeneous assay) is a method as a method in which measurement is always performed in a solution state. As measurement at high sensitivity has been demanded, however, a method of reacting an antigen and an antibody, separating a free labeled antibody (or antigen) not participating in the reaction by a cleaning operation (B/F separation) and then measuring the antigen-antibody complex, that is, a heterogeneous measuring method (heterogeneous assay) has been utilized generally. At present, a homogeneous assay at high sensitivity has become possible by developing a combination of a fluorescent dye and its quencher (quenching dye), or an FRET method of detecting the fluorescence of a second substance due to excitation by energy transfer from a first fluorescent substance to the second fluorescent substance, an LOCI method of applying oxygen channeling, a gold particle method of measuring different color formation due to approaching and agglutination of colloidal gold particles, etc.

Patent document 1 shows a method of disposing first metal particles and second metal particles on a substrate at a distance not causing interaction with each other, supplying the second metal particles having the first metal particles and a first substance bonded to the first metal particles and bonded to a second substance to the substrate, bonding the first metal particles and the second metal particles by way of the bonding between the first substance and the second substance, causing interaction to each other, and observing the bonding between the first substance and the second substance. Patent document 2 shows a method of quantitatively determining the amount of a specimen to be detected by measuring the fluorescence intensity based on the antigen-antibody reaction between a detected specimen-dye complex of a specimen to be detected (antigen) bonded with a not-fluorescent dye and an antibody to the detected specimen-dye complex which recognizes both of the specimen to be detected and the dye as epitopes, and the detected specimen-dye complex and the antibody.

Any of the methods is far from practical use for measuring a specific reaction while realizing high sensitivity and a further development is necessary, since it is necessary to provide special metal particle, substrate, dye, and antibody that recognizes two epitopes, and special techniques are required in the preparation of the system.

PRIOR ART DOCUMENT

Patent Document

Patent document 1: JP-A-2003-14765
Patent document 2: JP-A-2007-171213

SUMMARY OF THE INVENTION

Problem to be Solved by the Invention

A homogeneous measuring method (homogeneous assay) for realizing measurement at high sensitivity has been demanded for the method of performing the measurement always in the solution state in the prior art described above. Along with such a trend, a homogeneous assay at high sensitivity has become possible by developing a combination of a fluorescent dye and its quencher (quenching dye), or an FRET method of detecting the fluorescence of a second substance by excitation due to energy transfer from a first fluorescent substance to the second fluorescent substance, an LOCI method of applying oxygen channeling, a gold particle method of measuring different color formation due to approaching and agglutination of colloidal gold particles.

Factors for instabilizing the analysis based on the antigen-antibody reaction are as follows: the effect due to heterophilic antibody, false-positive due to non-specific reaction with blocking agent, etc., increase in the background due to the non-specific reaction with a labeled enzyme, false-negative in the case of the prozone phenomenon or high dose huck, false-negative or false-positive due to the effect of the property of samples such as high protein sample, milky serum sample, etc. false-positive or false-negative due to crossed reaction when a recombinant antibody is used, false-positive due to the crossed reaction in FSH, TSH, and LH, instability for the result of judgment due to the difference of measurement sensitivity between reagents, etc.

Further, fluorescence or luminescence exhibiting interference shows that assay is performed as if objects to be measured are present in the sample although the objects to be measured are not originally contained in the sample to possibly result in erroneous judgment and, further, this remarkably lowers the minimum detection limit of the measuring apparatus.

It is an object of the present invention to perform assay at high sensitivity when assay is performed based on the antigen-antibody reaction of a sample in an analytic method or apparatus due to fluorometry or luminometry while eliminating or effectively excluding the detection or measurement of non-specific fluorescence or luminescence such as interference light irrespective of the property of the sample or the level of the concentration of the substance contained in the sample.

Further, an object of the invention is intended to perform rapid assay based on the antigen-antibody reaction of a sample in an analytic method or apparatus due to fluorometry or luminometry while eliminating or effectively excluding the detection or measurement of non-specific fluorescence or luminescence such as interference light for the level of the concentration of the substance to be analyzed contained in the sample.

Further, an object of the invention is to quantitatively measure the concentration of the substance to be analyzed rapidly and at high sensitivity based on the antigen-antibody reaction of a sample in an analytic method or apparatus due to fluorometry or luminometry while effectively estimating the property of the sample or the level of the concentration of the substance other than the analyzed substance contained in the sample.

Means for Solving the Problem

When assay is performed based on the antigen-antibody reaction of a sample due to fluorometry or luminometry in an analytic method or apparatus, the invention can perform assay at high sensitivity while eliminating or effectively excluding the detection or measurement of non-specific fluorescence or luminescence such as interference light irrespective of the property of the sample or the level of the concentration of the substance contained in the sample.

When assay is performed based on the antigen-antibody reaction of a sample due to fluorometry or luminometry in an analytic method or apparatus, the invention can perform rapid assay while eliminating or effectively excluding the detection or measurement of non-specific fluorescence or luminescence such as interference light for the level of the concentration of the substance contained in the sample.

Further, when assay is performed based on the antigen-antibody reaction of a sample due to fluorometry or luminometry in an analytic method or apparatus, the invention can perform quantitative analysis rapidly and at high sensitivity while effectively estimating the property of the sample or the level of the concentration of other substances than the substances contained in the sample based on the antigen-antibody reaction.

Effect of the Invention (1) According to the present invention, when assay is performed based on antigen-antibody reaction of a sample due to fluorometry or luminometry in an analytic method or apparatus, assay can be performed rapidly while eliminating or effectively excluding the detection or measurement of non-specific fluorescence or luminescence such as interference light for the level of the concentration of the substance to be analyzed contained in the sample.

(2) Further, according to the invention, when assay is performed based on antigen-antibody reaction of a sample due to fluorometry or luminometry in an analytic method or apparatus, the concentration of the substance to be analyzed can be quantitatively determined rapidly and at high sensitivity while effectively estimating the property of the sample or the level of the concentration of other substances than the substance to be analyzed contained in the sample based on antigen-antibody reaction.

MODE FOR CARRYING OUT THE INVENTION

Examples of the present invention are to be described with reference to the drawings.

Embodiment 1

Figure 1:
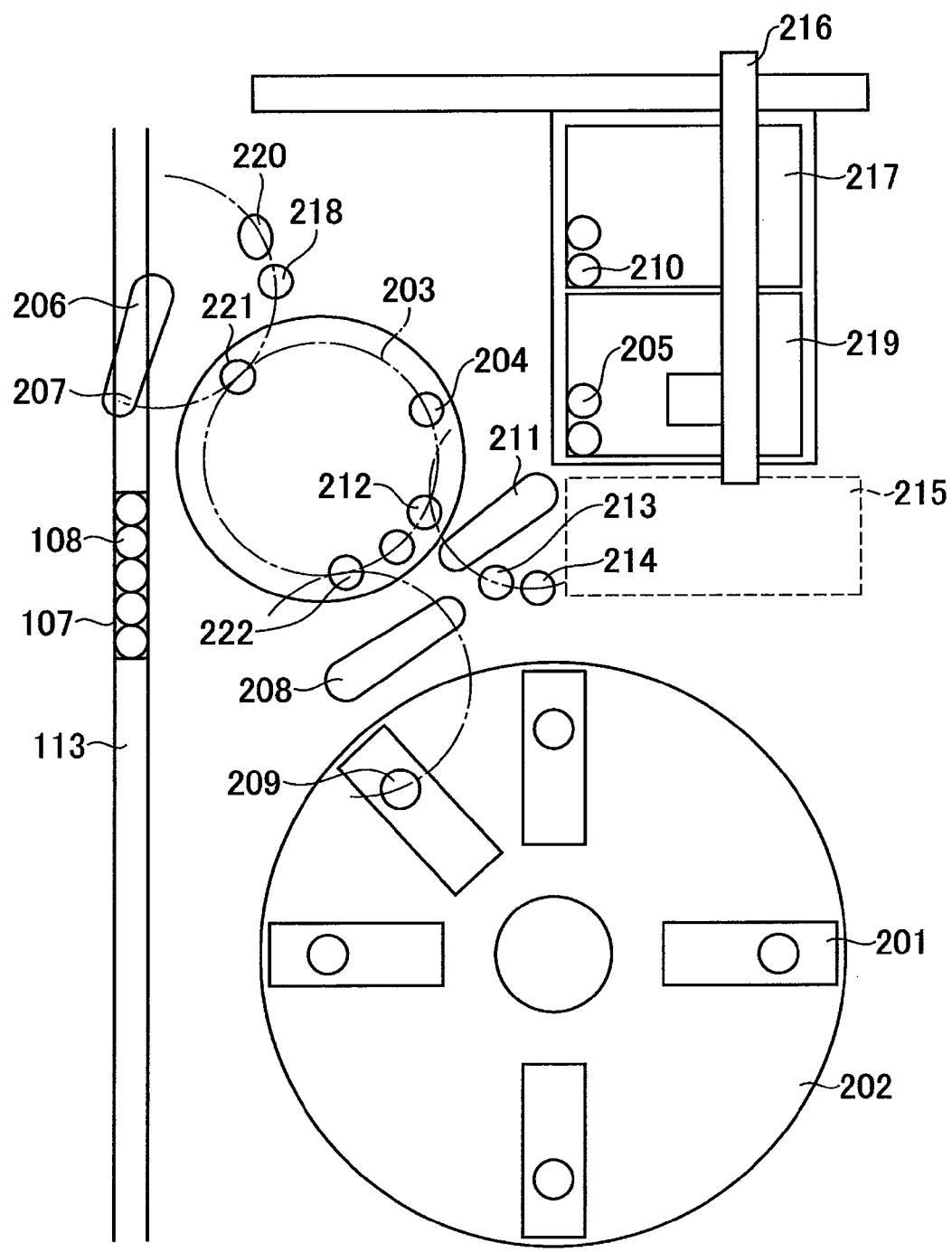
FIG. 1 is an example for the schematic appearance of an analyzer.

Referring to FIG. 1, a configurational example of an immunoassay unit 103 is to be described. In FIG. 1, reagent vessels 201 each contain a reagent solution corresponding to analysis items that can be analyzed by the immunoassay unit. The reagent vessels 201 are arranged on a reagent disk 202 rotatable as a reagent positioning device. A reaction disk 203 maintained at a constant temperature is operatively rotatable. A plurality of reaction positions are provided along the circumference on the reaction disk 203. Reaction vessels 205 from a reaction vessel storing position 219 are stored at the reaction positions. The reaction disk 203 moves, by the rotational operation, the reaction vessel 205 from a reaction vessel set position 204 to a specimen discharge portion 221, a reagent addition position 222, and a reaction solution suction position 212. A sample dispensing pipetter 206 can horizontally move a coupling tube coupling a disposable dispensing chip 210 from a position above the sample suction position 207 to a position above the sample discharge position 221 and, further, can also move vertically at respective positions. Prior to the suction of a sample, a disposable dispensing chip 210 is attached at the chip coupling position 218 to the top end of the chip coupling tube of the sample dispensing pipetter 206.

The reagent dispensing pipetter 208 can move from a position above a reagent suction position 209 on the reagent disk 202 to a position above the reagent addition position 222 and can also move vertically at respective positions. A shipper 211 can move for positions above a reaction solution suction position 212, above a buffer suction position 213, and above a cleaning solution suction position 214 for a flow cell and can also move vertically at respective positions. Further, the shipper 211 has a function of sending a reaction solution through a tube to the flow cell in a detection unit 215. A chip and a reaction vessel moving mechanism 216 capable of moving a grip portion in the direction x and the direction y moves the disposable dispensing chip 210 from a chip storing position 217 to the chip coupling position 218 and moves the disposable reaction vessel 205 from a reaction vessel storing position 219 to the reaction vessel set position 204. The reagent dispensing pipetter 208 and the shipper 211 are cleaned with water for the outer wall of the nozzle at each of cleaning positions corresponding to them respectively.

Then, a flow of processing in the immunoassay unit 103 is to be described. First, the reaction vessel move mechanism 216 moves the disposable dispensing chip 210 to the chip coupling position 218 and then moves the reaction vessel 205 to the reaction vessel set position 204. A rack 107 holding a sample container 108 is conveyed on a subline 113 such that the sample container 108 containing a sample to be analyzed is positioned at the sample suction position 207. At the same time, the reagent disk 202 rotates such that the reagent container 201 containing a reagent used for the analysis is positioned at the reagent suction position 209. At the same time, the reagent dispensing pipetter 208 moves to a position above the reagent suction position 209. The reagent dispensing pipetter 208 descends at the reagent suction position 209 and sucks the reagent into a pipette nozzle. Then, the reagent dispensing pipetter 208 ascends and moves to the nozzle cleaning position. When the pipette nozzle reaches a position above the nozzle cleaning position, cleaning water is blown from a cleaning tank to clean the top end of the pipette nozzle.

On the other hand, the sample dispensing pipetter 206 moves the dispensing chip 210 to a position above the sample suction position 207, and the dispensing chip 210 descends into the sample container 108 on the rack 107 and sucks a predetermined amount of a sample. After sucking the sample, the dispensing chip ascends and moves to the sample discharge position 221. Then, the dispending chip descends and discharges the sample sucked and kept in the dispensing chip into the reaction vessel 205. After discharging the sample the dispensing chip is raised by the sample dispending pipetter 206 and moved to a chip discarding position 220. At the chip discarding position 220, the sample dispensing pipetter 206 removes and discards the disposable dispensing chip 210 from the coupling tube at the chip discarding position 220.

After lapse of a predetermined time required for reaction, the shipper 211 moves a suction nozzle to a position above the buffer suction position 213, lowers the nozzle and sucks a buffer through the nozzle toward the flow cell. Then, the top end of the nozzle of the shipper 211 is cleaned at the nozzle cleaning position.

Then, the reaction disk 203 moves the reaction vessel 205 to the reaction solution suction position 212. The shipper 211 sucks the reaction solution at the reaction solution suction position 212 through the nozzle toward the flow cell. After sucking the reaction solution, the shipper 211 moves the nozzle to the buffer suction position 213 and sucks the buffer. The sucked buffer and reaction solution are sent through the tube to the flow cell in the detection unit 215 in which measurement is carried out. Then, the shipper 211 moves the nozzle to the cleaning solution suction position 214, sucks the cleaning solution for the flow cell and cleans the inside of the flow cell in the detection unit 215 by the cleaning solution.

Figure 2:
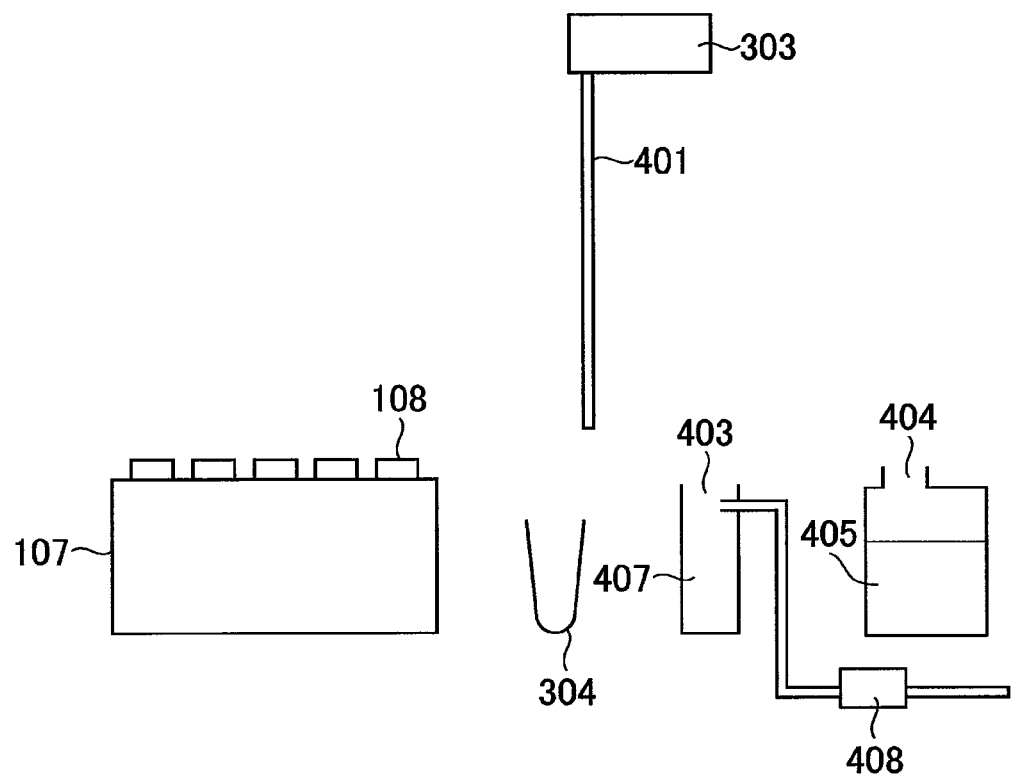
FIG. 2 is an example of an antigen-antibody reaction.

Then, a configuration example of an analysis unit 104 is to be described with reference to FIG. 2. In FIG. 2, a biochemical analysis unit 104 includes a reagent supply system having reagent disks 301A, 301B for holding a plurality of reagent containers 310 and reagent dispensing pipetters 302A, 302B, a sample supply system having a sample dispensing pipetter 303, a reaction unit having a reaction disk 305 for holding a plurality of reaction vessels 304, and a measuring system having a multi-wave length photometer 306 and an analog/digital converter 307.

In FIG. 2, the rack 107 holding the sample containers 108 is moved from a moving unit 102 to a sample suction position 308 on a subline 115. The sample dispensing pipetter 303 sucks a predetermined amount of a sample in the sample container 108 into a pipette nozzle 401 and discharges the sample into a reaction vessel 304.

The reaction vessel 304 to which the sample solution is discharged and dispensed is moved to a first reagent addition position by the rotation of the reaction disk 305 whose temperature is kept by a thermostatic bath 309. In this step, the reagent disk 301A also moves so as to position the reagent container 310 corresponding to the analysis item of a sample brought to the reagent addition position by the rotational operation to the reagent suction position.

Then, a predetermined first reagent sucked by the pipetter nozzle of the sample dispensing pipetter 302A is added to the reaction vessel 304 moved to the first reagent addition position. The reaction vessel 304 after addition of the first reagent is moved to the position of a stirring device 311 in which first stirring is performed. In the case of analysis item requiring addition of a second reagent, the second reagent is further added by the reagent dispensing pipette 302B and the content is stirred.

The reaction vessel 304 containing a reaction solution comprising the sample and the reagent in admixture is moved so as to traverse an optical flux from a light source, and light transmitting the reaction vessel is incident to a multi-wavelength photometer 306. Then, the absorption of the reaction solution as the content in the reaction vessel 304 is detected by the multi-wavelength photometer 306. The detected absorption signal is supplied by way of the analog/digital (A/D) converter 307 and an interface to a control section 312 such as a computer and converted to the concentration of the analysis item as a measuring object in the sample. The reaction vessel 304 after completion of the assay is moved to a position where a reaction vessel cleaning mechanism (not illustrated) is provided, and cleaned with water after discharge of the reaction solution in the reaction vessel, followed by the next analysis.

Method of enabling continuous measurement or measurement for plural times is to be described below.

Figure 3:
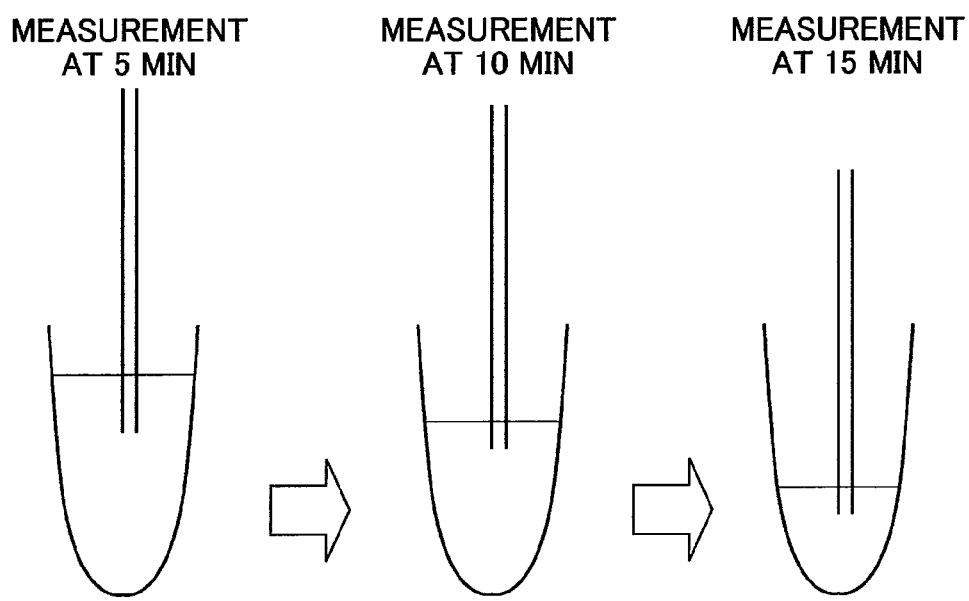
FIG. 3 is a schematic view in the case where a reaction solution from a reaction vessel is sampled at a predetermined time and luminometry or fluorometry proceeds successively.

FIG. 3 shows successive sampling of a reaction solution from one reaction vessel and performing measurement for luminescence value by using them. Luminometry is performed by sampling a predetermined amount of a reaction solution upon each measurement for luminescence amount. Reaction is continued for the reaction solution remaining in the vessel and the solution is kept in an incubator till the final luminometry. The reaction solution may be sampled with the vessel placed in the incubator or the solution may be sampled by taking out the vessel from the incubator. If the composition of the reaction solution during incubation is deviated, it is desirable to sample the reaction solution after the solution is stirred and mixed.

Figure 4:
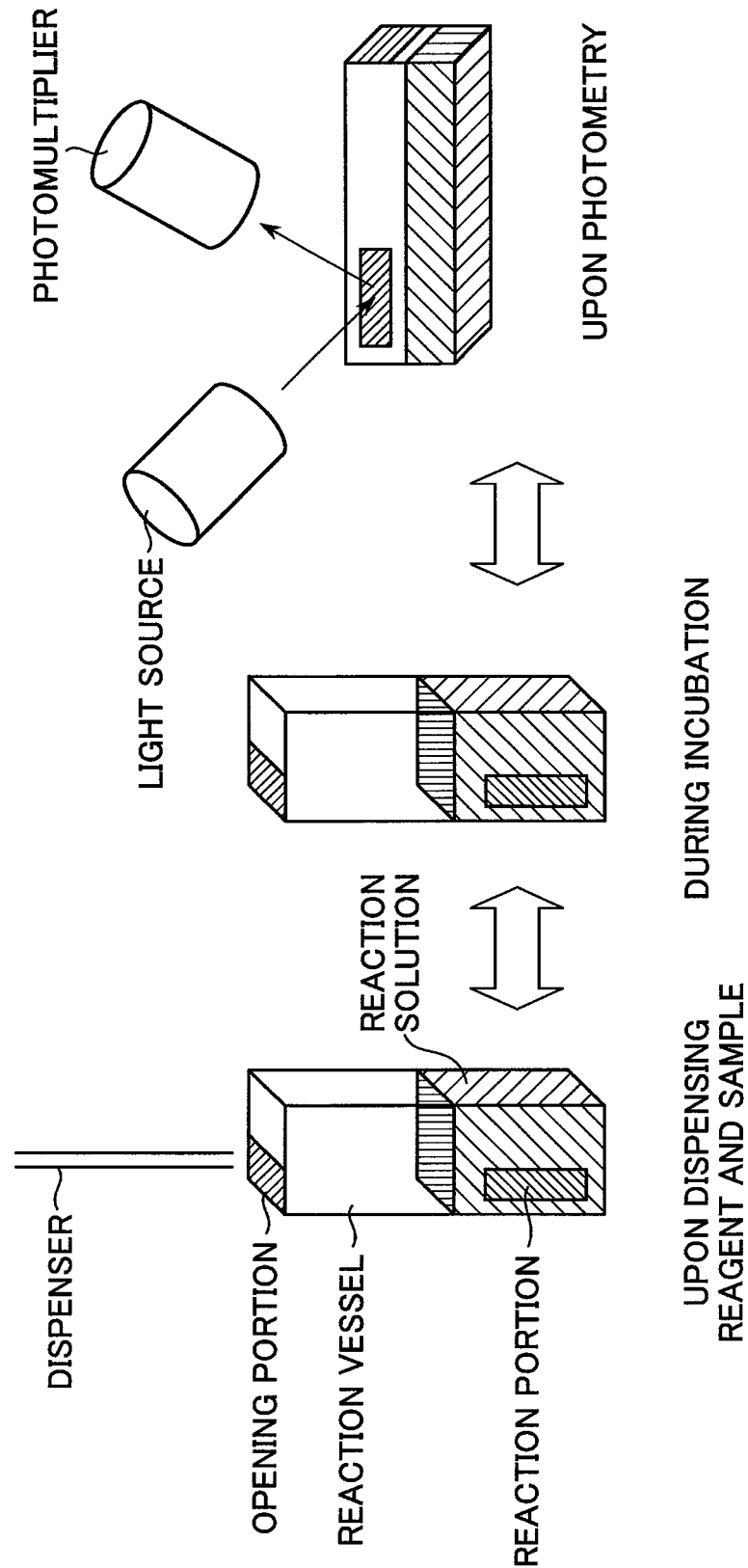
FIG. 4 is a reference schematic view in the case where luminometry or fluorometry proceeds at every predetermined time without sampling of the reaction solution in a reaction vessel.

FIG. 4 illustrates an example in which luminometry is performed with time or on every predetermined time without sampling of the reaction solution in the reaction vessel. The vessel is formed with an opening, through which a sample or a reagent is dispensed into the vessel. On the other hand, the vessel partially or entirely has a portion in which an antibody, an antigen, or other substance that traps a measuring object is immobilized, and the reaction proceeds at the portion. When particles, etc. for immobilization are present in the reaction solution and the reaction proceeds on the particles, the portion for immobilization to the vessel is not necessarily provided. FIG. 4 shows that the portion for immobilization is separated upon luminometry from the reaction solution by tilting the vessel, and luminometry is performed at the portion. In the reaction solution, unreacted fluorescence labeled substance such as a fluorescent dye-labeled antibody not yet reacted in the portion for immobilization may possibly be present. When luminometry or fluorometry is performed by using the solution containing the same, background increases during measurement due to luminescent or fluorescent generated from the unreacted labeling substance. Therefore, this may possibly bring about a hindrance when measurement is attained at higher sensitivity and it is desirable to adopt a method of removing the background as much as possible. A reaction curve can be obtained by repeating the luminometry and continuation of the reaction by returning the container to an original state and contacting the portion for immobilization to the reaction solution, whereby more rapid and exact analysis for measuring object than that shown in Example 3 can be performed.

The more the number of times for the luminometry is better and real time measurement is desirable. It can be seen that when a measured value is obtained in the midway even for once in addition to the final measurement, more rapid and accurate reliable analysis that can circumvent the need to re-test is performed, thereby providing a remarkable merit on the disease diagnosis.

Figure 5:
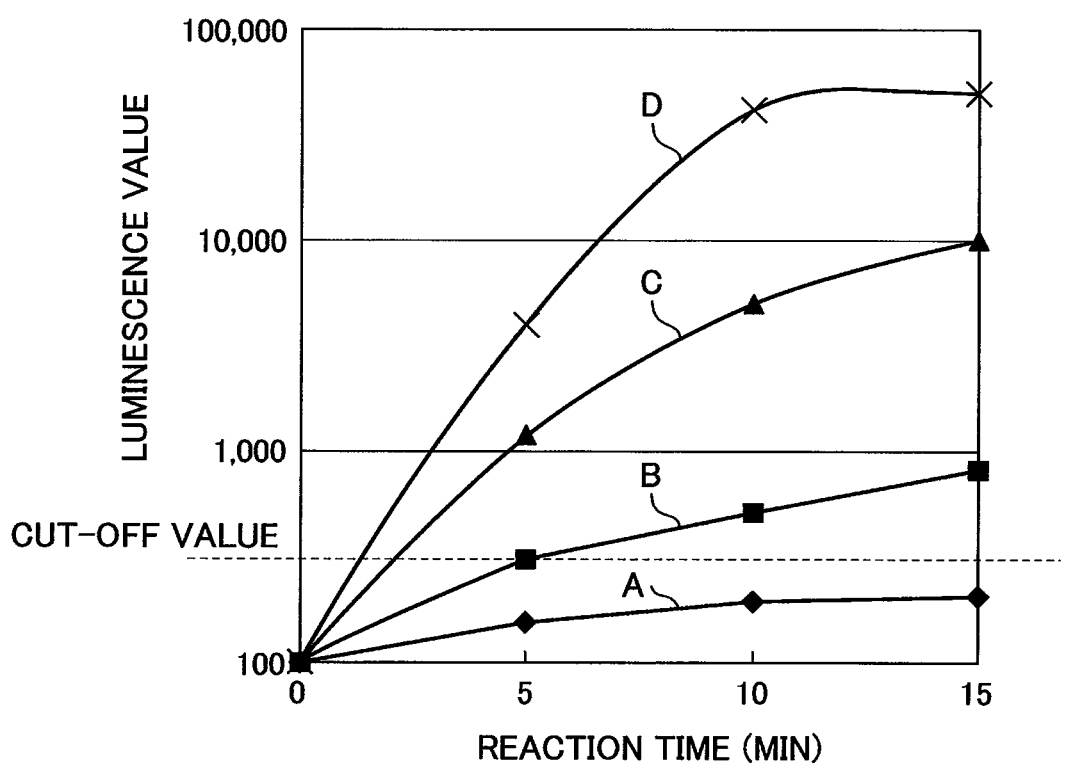
FIG. 5 is an example of a reaction curve with time (1).

FIG. 5 shows an example of a signal curve with time for antigen-antibody reaction. Generally, while a luminescence value or a signal increases along with progress of the reaction, increment of the luminescence value becomes smaller after lapse of a predetermined time. It is determined that the reaction is completed at this point, the luminescence value is measured and it is judged whether an antigen or an antibody is contained or not contained in the sample to be detected. A reference value or a boundary value in this point is referred to as a cut off value and it is judged as positive when a larger luminescence value than the reference value is obtained and judged as negative when it is less than the reference value (qualitative measurement). The vicinity of the cut off value is defined as a gray zone in which the judgment is regarded as impossible and re-measurement is sometimes demanded. Further, the luminescence value is sometimes compared to a calibration curve and the amount of the measuring object is described quantitatively (quantitative measurement). In the example of FIG. 5, the antigen-antibody reaction is completed at a reaction time of 15 minutes, the luminescence value is measured, and qualitative measurement is conducted as to whether the value is more than or less than the cut off value, or the luminescence value is compared to a calibration curve to obtain a read value for the amount of the contained measuring object. A is not more than the cut off value and judged as negative, and B, C and D are judged as positive. Alternatively, a read value is obtained based on a calibration curve and served for diagnosis.

Advantages in obtaining the luminescence value with time for plural times are shown in comparison with an existent method of ending the reaction at 15 minutes or upon ending of the reaction and sampling the luminescence value for once. When measurement for luminescence values is performed at the initial time or after lapse of 5 minutes, it can be seen that values of samples C and D are more than the cut off value and the samples C and D are judged positive. On the other hand, in the samples A and B, while it is desired that measurement for luminescence value or photometry can be performed continuously, the advantage increases since measurement can be performed twice or plural times in the course of the reaction.

The following shows cases in which luminescence values are obtained with time for negative or slightly positive samples. It is judged that E is negative and F and G are positive at 15 minutes. For G, it is judged positive also at 10 minutes and early judgment for the result is possible without waiting for 15 minutes at the final time. While F can be judged positive at 15 minutes, it can also be estimated to be positive at 15 minutes considering the measurement at 5 minutes and 10 minutes together and early estimation is possible. Further, the result at 15 minutes can be supported by the result at 5 minutes and 10 minutes and the final judgment becomes more reliable.

Figure 6:
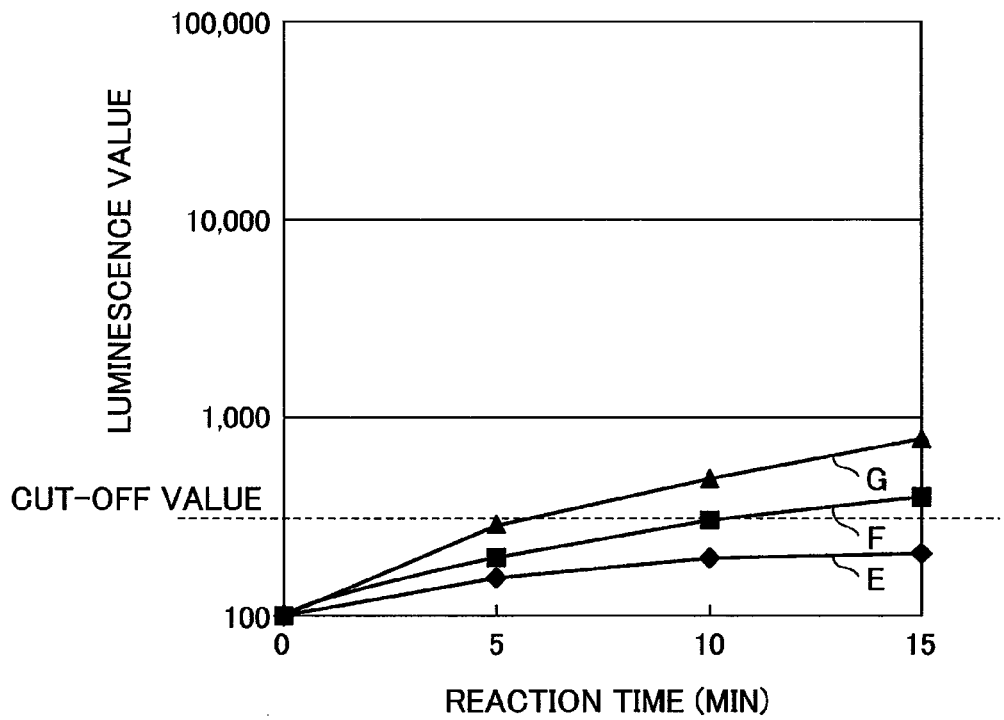
FIG. 6 is an example of a reaction curve with time (2) in the case where a low value sample is used.

Then, FIG. 6 shows a case where measuring objects are contained from medium to large amount relatively. Each of H, I, G is judged positive at 5 minutes and the result of judgment could be recognized in an early stage after starting the test. The result can be informed more rapidly to a doctor. If, for example, a patient suffers from heart disease and requires rapid treatment such as for cardial infarction, a possibility of escaping death increases by starting effective medical treatment at an early stage.

Figure 7:
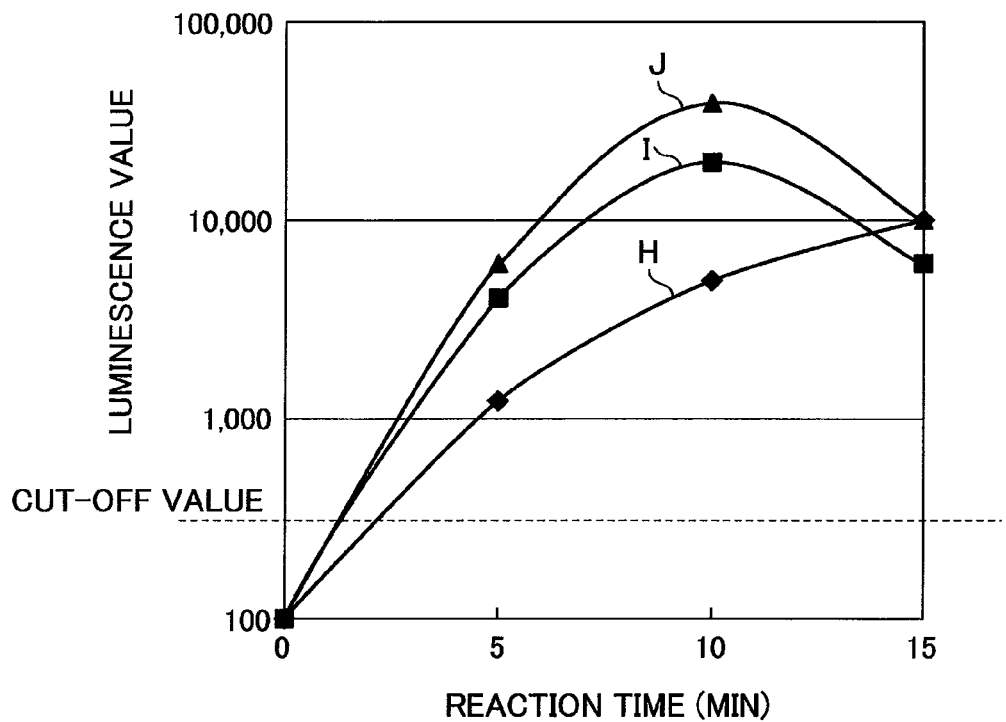
FIG. 7 is an example of a reaction curve with time (2) in the case where a high value sample is used.

In an antigen-antibody reaction or an analyzer therefor, there may be a possibility of such a case that a small luminescence value is shown and, in an extreme case, a sample is judged to be negative although a great amount of measuring objects are actually contained in the sample. That is, when a great amount of measuring objects are contained, which are called as zone phenomenon, prozone, post zone or high dose huck, or when a great amount of the labeling substances such as fluorescent dyes are contained and, further, when the balance of ratio between the capture antibody and the labeling antibody in the antigen-antibody reaction is not balanced well. In such cases, the positive judgment is sometimes possible by recognizing the luminescence value in the initial stage of reaction and the luminescence value herein may sometimes reflect the amount of the measuring object more appropriately than that at the final measurement. In FIG. 7, upon final measurement at 15 minutes, the measured luminescence value is read as H=J>I, and it is also read as H=J>I based on the calibration curves, and the sample H is judged as a sample of high value containing more measuring objects than the sample I. However, in view of the luminescence values at 5 minutes or 10 minutes, it is read as: J>I>H, and it has been found that the sample J contains the greatest amount of the measuring objects.

DESCRIPTION OF REFERENCE NUMERALS 103 immunoassay unit
201 reagent container
202 reagent disk
203 reaction disk
205 reaction vessel
206 sample dispensing pipetter
208 sample dispensing pipetter
210 dispensing chip
211 shipper

The invention claimed is:

1. An automatic analyzer comprising:
a reaction vessel to contain a reaction solution including antigens and antibodies for an antigen-antibody reaction,
where luminescent labels are bonded to one of the antigens, the antibodies or another substance in the reaction solution directly or indirectly, the reaction vessel includes a portion which collects carriers formed with antigen-antibody bonding present in the reaction solution from the antigen-antibody reaction, the carriers including the luminescent labels;
a measuring mechanism to detect light generated from the carriers collected on the portion of the reaction vessel; and
a moving mechanism to move the reaction vessel to a measurement position and the portion of the reaction vessel which has collected the carriers formed with the antigen-antibody bonding are separated from a remainder of the reaction solution so that the measuring mechanism detects the light from the portion of the reaction vessel,
wherein the moving mechanism moves the reaction vessel to the measurement position a plurality of times after starting the antigen-antibody reaction so that the measuring mechanism quantitatively measures the antigen-antibody reaction in time series, and
wherein the concentration of carriers collected at the portion of the reaction vessel changes over the time series.

2. The automatic analyzer according to claim 1, further including:
a calculation mechanism for calculating the antigen-antibody reaction with time based on the result of the time series measurement by the measuring mechanism.

3. The automatic analyzer according to claim 1, further including:
a removing mechanism for forming the carries from the antigen-antibody bonded reaction which are labeled with the luminescent label, and removing the remainder of the reaction solution which has yet to form the antigen-antibody bonding in the reaction vessel.

4. The automatic analyzer according to claim 1, wherein the moving mechanism samples the reaction solution in the reaction vessel in the time series.

5. The automatic analyzer according to claim 1, wherein the portion is disposed on a side surface of the reaction vessel.

6. An analyzing method comprising:
providing a reaction vessel with a reaction solution including antigens and antibodies for an antigen-antibody reaction, where luminescent labels are bonded to one of the antigens, the antibodies or another substance in the reaction solution directly or indirectly;
starting an antigen-antibody reaction in the reaction vessel;
collecting carriers formed with antigen-antibody bonding present in the reaction solution from the antigen-antibody reaction at a portion of the reaction vessel, where the carriers include the luminescent labels; and
repeatedly moving the reaction vessel to a measurement position and the portion of the reaction vessel which has collected the carriers formed with the antigen-antibody bonding are separated from a remainder of the reaction solution and detecting light generated from the carriers collected on the portion of the reaction vessel so that the antigen-antibody reaction is quantitatively measured at least two times in a time series,
wherein the concentration of carriers collected at the portion of the reaction vessel changes over the time series.

7. The analyzing method according to claim 6, further comprising:
calculating the antigen-antibody reaction with time based on the result of the time series measurement.

8. The analyzing method according to claim 6, further comprising:
removing the remainder of the reaction solution which has yet to form the antigen-antibody bonding not present on the carrier in the reaction vessel.

9. The analyzing method according to claim 6, further comprising:

sampling the reaction solution in the reaction vessel in the time series.

10. The analyzing method according to claim 6, wherein the portion is disposed on a side surface of the reaction vessel.

* * * * *